United States Patent [19]

Wolf et al.

[11] 4,227,018
[45] Oct. 7, 1980

[54] ODORLESS BENZOIC ACID PROCESS

[75] Inventors: Wilhelm Wolf, Krefeld; Meinhard Puhl, Neumorschen, both of Fed. Rep. of Germany

[73] Assignee: Bayer Aktiengesellschaft, Leverkusen, Fed. Rep. of Germany

[21] Appl. No.: 637,546

[22] Filed: Dec. 4, 1975

[30] Foreign Application Priority Data

Dec. 21, 1974 [DE] Fed. Rep. of Germany ....... 2460822

[51] Int. Cl.³ .............................................. C07C 51/42
[52] U.S. Cl. .................................................. 562/494
[58] Field of Search ........................... 260/525, 524 R; 562/494

[56] References Cited

U.S. PATENT DOCUMENTS 3,210,416  10/1965  Fragen et al. .................. 260/524 R
3,309,289  3/1967  Messina et al. ...................... 260/525

FOREIGN PATENT DOCUMENTS 824367  11/1959  United Kingdom ..................... 260/525

OTHER PUBLICATIONS

Weissberger, "Separation and Purification", part 1, 2n ed. (1956) pp. 817-829.

Primary Examiner—A. Siegel
Attorney, Agent, or Firm—Sprung, Felfe, Horn, Lynch & Kramer

[57] ABSTRACT

Odorless benzoic acid is prepared by treating benzoic acid, after crystallization, with an inert gas at temperatures in the range of 50°–100° C. The process is best carried out using benzoic acid crystals or particles having a particle size of less than 1 mm in a moving or fluidized bed.

10 Claims, No Drawings

ODORLESS BENZOIC ACID PROCESS

BACKGROUND

This invention relates to a process for the manufacture of practically odourless benzoic acid by treatment with an inert gas at an elevated temperature.

Benzoic acid is manufactured on a large scale by oxidation of toluene with air (Ullmanns Enzyklopädie der technischen Chemie (Ullmann's Encyclopedia of Industrial Chemistry), 4th edition, volume 8, pages 366–370 (1974)). At the same time, by-products such as diphenyl and o-, m- and p-methyldiphenyl, hereafter conjointly designated as diphenyls, are formed, which, because of their strong odour, are objectionable even in small amounts, particularly if the benzoic acid is used and further processed, for example to give benzoic acid esters, which are used as plasticisers, dyestuff carriers, cosmetics and pharmaceuticals.

In the course of the customary working up of the reaction mixture obtained on oxidation of toluene with air, the diphenyls are not removed completely. Odourless benzoic acid can only be obtained by sublimation or recrystallisation with the aid of adsorbents, for example active charcoal, or by purification via sodium benzoate. Purification by distillation is technically virtually impossible, since diphenyl forms an azeotrope with benzoic acid, which only boils 4° C. lower than benzoic acid itself. Because of the low solublity in water, recrystallisation from water is also not an industrially usable method. Even when the benzoic acid is processed further, the diphenyls are in many cases not removed automatically in the course of this processing, so that the end products also continue to exhibit the odour which, when they are used, is at times even more objectionable.

There is thus an urgent need for practically odourless benzoic acid, that is to say a benzoic acid of very low content of diphenyls, but hitherto no method achievable with simple technical means was available for satisfying this need.

In general benzoic acid is obtained, after manufacture and removal of unconverted starting material and of easily removable by-products by distillation or extraction, in the form of the melt, from which it is then obtained in the form of crystallised flakes, for example by using cooling rollers. There is also a great demand for benzoic acid in a finely divided form, which can only be obtained with difficulty by grinding, since benzoic acid shows an exceptional tendency to cake together after grinding.

SUMMARY

It has now been found that benzoic acid is obtained practically odour-free if, after crystallisation, it is treated with an inert gas at an elevated temperature. This results in a decrease in the content of diphenyls to below 0.01% by weight and virtual freedom from odour.

At the same time, the temperature must of course be below the melting point of benzoic acid while on the other hand it is desirable to select a temperature above the melting point or mixed melting point of the diphenyls. In general, the treatment is carried out in the temperature range of 50° to 100° C., preferably between 70° and 90° C.

DESCRIPTION

A suitable procedure is to blow warm inert gas from below into a vertical drying tower, into which the benzoic acid has been filled and is heated to the appropriate temperature, and withdraw the gas at the top. Of course, the gas can also be recycled and the diphenyls and vaporised or entrained benzoic acid removed from the main stream or from a part-stream of the gas, for example by cooling, adsorption, for example with active charcoal, or, in the case of benzoic acid, washing out with basic solutions or solvents.

Of course, other designs of apparatus can also be chosen for the process according to the invention, for example placing the benzoic acid on drying trays in a drying oven through which inert gas flows, or placing it on perforated trays in a drying tower through which inert gas flows upwards. However, treatment in a completely filled drying tower has proved particularly suitable because of the simplicity of filling and emptying.

The end of the requisite treatment with inert gas can be easily ascertained from a sample of the benzoic acid by customary analytical methods such as gas chromatography or by an odour test. In general, a duration of treatment with inert gas of at least 6 hours up to about 20 hours is required in a drying tower; preferably, the treatment is carried out over a period of 8 to 12 hours.

Of course, the treatment with the inert gas first results in an appropriate lowering of the content of diphenyls in the immediate vicinity of the point of entry, whilst in more remote parts of the apparatus the content may be increased further as a result of adsorption processes. Hence, adequate duration of treatment is important; the treatment must continue until the desired purification effect is achieved for the entire amount of benzoic acid. The purification effect might be described as progressing in zones; it follows from this that an appropriate period of time is required to reach the final zone of the apparatus. However, this period of time in general depends on the size and nature of the apparatus used and on the amount of benzoic acid, so that it is not possible to make general statements about it. Depending on the circumstances relating to the apparatus, the period may amount to minutes or hours.

In addition to the duration of the treatment, the temperature is of essential importance, as follows from what has been stated above.

On the other hand, the amount of inert gas per kg of benzoic acid is of lesser importance. It is suitably chosen to lie in the range of about 200 to about 500 l of gas, preferably 300 to 400 l of gas, per kg of benzoic acid and per hour.

It is assumed from these facts that the diffusion of the diphenyls from the interior of the benzoic acid flakes and particles to the surface is the rate-determining step, whilst the vaporisation of the diphenyls at the surface of the particles and the removal of the diphenyls with the inert gas takes place more rapidly.

As the inert gas it is possible to use any desired gas which does not react with benzoic acid, for example nitrogen, carbon dioxide, noble gases or a mixture of different gases. Because of the hazard of dust explosions, air is in general not a suitable inert gas. However, an air/nitrogen mixture of which the oxygen content is less than 8% by volume, this being the limit below which dust explosions need no longer be feared, is particularly appropriate.

Further, it has been found that the treatment, according to the invention, of benzoic acid with inert gas at an elevated temperature can be carried out particularly advantageously if it is effected with benzoic acid crystals or particles which have a particle size of less than 1 mm, preferably of between 0.25 and 0.75 mm, in a moving bed or fluidised bed.

Benzoic acid crystals or particles of the stated particle size are furthermore obtained particularly advantageously if the molten benzoic acid is subjected to spray crystallisation.

This spray crystallisation has not previously been disclosed for benzoic acid but is described, for example, for diphenylolpropane (bisphenol A) in DT-OS No. (German Published Specification) 1,643,536. The spray crystallisation is carried out in the manner of a spray drying process; the spray drying process, and the spray driers required for it, form part of the state of the art (compare Ullmanns Enzyklopädie der technischen Chemie, 4th edition, volume II, (1952), pages 712-713). Equally, the one-component nozzles required for the purpose are known and form part of the state of the art (loc. cit., pages 254 and 255).

In general, the small droplets of molten benzoic acid which issue from the one-component nozzle are allowed to crystallise whilst falling under gravity in counter-current to a cold inert gas. The cold gas serves as a coolant for cooling the melt and removing the heat of crystallisation.

The construction of the apparatus for the process according to the invention is known to experts from the state of the art of spray drying.

Thereafter, the crystals can be treated particularly advantageously-without further cooling-with warm air in a moving bed or fluidised bed in the manner according to the invention.

To maintain the moving bed or fluidised bed, an amount of inert gas greater than that mentioned above may be appropriate or necessary. In general, the amount will appropriately be between 5,000 and 15,000 l of gas per kg of benzoic acid and per hour.

Of course, an interim further cooling is also possible but is not advantageous because of the need subsequently to heat the material again to the temperature used in the treatment with inert gas.

By using the spray crystallisation according to the invention, the duration of the treatment with inert gas can be shortened substantially; in general, a mean residence time of the spray-crystallised benzoic acid in the moving bed or fixed bed of only up to 60 minutes is required. The mean residence time is suitably chosen to be in the range from 8 to 30 minutes, especially 10 to 15 minutes.

The surprising advantages of the process according to the invention are that a practically odourless benzoic acid containing less than 0.01% by weight of diphenyls is achieved, expensive purification operations are rendered superfluous and little time is required.

EXAMPLE 1

150 kg per hour of molten benzoic acid are sprayed through a one-component nozzle in a 10 m high tower of 1,200 ml diameter; at the same time, a gas mixture of 38 parts by volume of air and 62 parts by volume of nitrogen is blown into the tower from below, at a temperature of 20° to 30° C. and in an amount of 1,200 m³/hour.

Spherical crystals are thereby obtained, of which the average diameter of one-third of the amount is in the range between 0.1 and 0.5 mm and that of two-thirds of the amount is in the range between 0.5 and 1 mm.

EXAMPLES 2 TO 6

Benzoic acid which contained about 0.15% by weight of impurities was used in these examples; the impurities were composed of 0.015% by weight of o-methyl-diphenyl, 0.06% by weight of m- and p-methyl-diphenyl, 0.04% by weight of diphenyl, 0.02% by weight of benzyl benzoate and 0.01% by weight of unidentified impurities.

This benzoic acid was employed in the form of about 0.4 mm thick flakes and, alternatively, in the form of almost spherical crystals obtained by spray crystallisation, the proportion of particles of 0.1-0.25 mm diameter being 6%, the proportion of particles of 0.25-0.5 mm diameter being 31%, the proportion of particles of 0.5-0.75 mm diameter being 45% and the proportion of particles of 0.75-1.0 mm diameter being 18%.

EXAMPLES 2 AND 3

200 g of benzoic acid either in the form of flakes or in the form of almost spherical crystals obtained by spray crystallisation were filled into a U-tube of 25 mm internal diameter, which was suspended in a water bath warmed to 80° C. Air prewarmed to 80° C. was blown through the U-tube from the end of one of the arms; after 8 hours the average amount of impurities was determined in each case, in the same manner as before beginning the experiment.

The experimental results are summarised in Table I which follows:

Table I

| Example No. | Benzoic acid (form) | l/hour | Air l (total) | Impurities |
|---|---|---|---|---|
| 2 | Flakes | 60 | 480 | 0.04% by weight |
| 3 | Spherical crystals (formed by spraying) | 60 | 480 | 0.01% by weight |

EXAMPLES 4 TO 6

50 g of benzoic acid were in each case filled into a funnel-shaped glass tube of 85 mm diameter at the upper, wide end and of conical angle 30°, the tube being suspended in a waterbath at 80° C. and air warmed to 80° C. being blown through it from the lower end. At the end of the blow-through period, the impurities were determined in the same manner as in the benzoic acid employed.

The experimental conditions and results are summarised in Table II which follows:

TABLE II

| Example No. | Benzoic acid (form) | Air l/hour | l (total) | Duration of experiment hours | End product % of impurities |
|---|---|---|---|---|---|
| 4 | Flakes | 400 | 100 | 0.25 | 0.04 |
| 5 | Spherical crystals (formed | 400 | 25 | 0.062 | 0.01 |

TABLE II-continued

| Example No. | Benzoic acid (form) | Air l/hour | l (total) | Duration of experiment hours | End product % of impurities |
|---|---|---|---|---|---|
| 6 | Spherical crystals (formed by spraying) | 400 | 50 | 0.125 | 0.00 |

What is claimed is:

1. Process for making substantially odorless benzoic acid which consists essentially of spray drying benzoic acid contaminated with diphenyl to obtain substantially spherical crystals of said benzoic acid and thereafter passing an inert gas selected from the group consisting of nitrogen, carbon dioxide, a noble gas or air having an oxygen content of less than 8% by volume or a mixture thereof at a temperature of 50°–100° C. through said benzoic acid spherical crystals contaminated with diphenyls.

2. Process of claim 1 wherein benzoic acid crystals of particle size less than 1 mm are used.

3. Process of claim 1 wherein benzoic acid crystals of particle size from 0.25 to 0.75 mm are used.

4. Process according to claim 1 wherein the inert gas is passed through the benzoic acid for a period of 6 to 20 hours.

5. Process according to claim 4 wherein the inert gas is passed through the benzoic acid for a period of 8 to 12 hours.

6. Process according to claim 1 wherein the inert gas is nitrogen.

7. Process according to claim 1 wherein the inert gas is air having an oxygen content of less than 8% by volume.

8. Process according to claim 1 wherein said inert gas is passed from below vertically upwards into a vertical drying tower containing the benzoic acid particles.

9. Process according to claim 1 wherein the benzoic acid is disposed on a drying tray in a drying oven and inert gas is passed therethrough.

10. Process according to claim 1 wherein the benzoic acid particles are disposed on perforated trays in a drying tower through which inert gas flows upwardly.

* * * * *